United States Patent [19]
Erb

[11] 4,007,249
[45] Feb. 8, 1977

[54] METHOD OF FORMING A REMOVABLE CERVICAL CAP

[75] Inventor: Robert Allan Erb, Schuylkill Township, Chester County, Pa.

[73] Assignee: The Franklin Institute Research Laboratories, Philadelphia, Pa.

[22] Filed: July 15, 1974

[21] Appl. No.: 488,584

[52] U.S. Cl. .............................. 264/222; 128/127; 128/131; 264/DIG. 30
[51] Int. Cl.² ...................... B29C 1/14; A61F 5/46
[58] Field of Search .................... 264/222, DIG. 30; 128/131, 127

[56] References Cited
UNITED STATES PATENTS

| | | | |
|---|---|---|---|
| 2,691,192 | 10/1954 | Bent | 264/294 |
| 3,344,220 | 9/1967 | Cook | 264/222 |
| 3,440,314 | 4/1969 | Frisch | 264/222 |
| 3,833,701 | 7/1974 | Johnson et al. | 264/222 |

*Primary Examiner*—Donald J. Arnold
*Attorney, Agent, or Firm*—Dorfman, Herrell and Skillman

[57] ABSTRACT

A removable elastomeric cervical cap includes a thin-walled cap-shaped member having the same shape as the exocervix and having an inside surface conforming identically to the exocervix surface. The method includes expanding the vaginal wall to substantially expose the exocervix surface. A layer of a liquid self-curing elastomeric material is then applied to only the exocervix surface, the inner surface of the layer conforming identically to the surface without distorting the surface. The liquid elastomeric material is then permitted to solidify.

13 Claims, 19 Drawing Figures

METHOD OF FORMING A REMOVABLE CERVICAL CAP

This invention relates to a novel cervical cap for the prevention of fertilization of a human female and is particularly concerned with a cervical cap having an inside surface conforming identically to the exocervix surface.

The use of cervical caps was first described by F. A. Wilde in 1838 in *Das weibliche Gebär-Unvermögen*, Berlin. Since that time many types of cervical caps have been mass produced. Included in the mass produced caps are: (1) the vault cap which is a hemispherical rubber or plastic cap having a thin center and a thick rim. It is made in sizes 50 to 74 mm in diameter; (2) the check pessary cap which is a thimble-shaped rubber cap with a thick base and which may include a string attached thereto for removal. It is made in sizes 22 to 31 mm in diameter; (3) the plastic ortho cervical cap which is rigid. It is made in different standard sizes; and (4) the vimule cap which is made of rigid rubber and includes a flanged base to increase the degree of suction when the cap is used. It is made in sizes 42 and 55 mm in diameter. In general, the prior cervical caps did not precisely fit the exocervix. The imprecise fit did not insure retention of the cervical cap on the exocervix nor did it insure that sperm transport around the cervical cap could not occur thereby resulting in an unreliable birth control method. This is presently confirmed in that cervical caps are relegated a minor place among the known birth prevention devices.

Also in *Das weibliche Gebär-Unvermögen* a pertinent portion suggests making a cervical cap from a special wax impression of the vaginal portion of the cervix. In the suggested method, a wax impression must first be prepared from the cervix, the wax impression is then used to make a mold of the cervix and then a cervical cap is made from the mold of the cervix. Since it is very difficult to make a wax impression of soft human tissue, a cervical cap formed from a mold made from the wax impression of the cervix cannot have an identical negative-image cervix-conforming inside surface. In addition the wax impression of the cervix can become distorted during removal from the cervix or from a subsequent mold making step. In either case there is not adequate assurance that the cervical cap formed by the suggested method will achieve 100% birth control prevention when properly used. Since 1838 when the suggested method was proposed a further reference to its actual use has not been found.

The novel removable elastomeric cervical cap includes a thinwalled cap-shaped member having the same shape as the exocervix and having an inside surface conforming identically to the exocervix surface. Identical negative-image conformity of the inside surface of the cervical cap and the exocervix surface is required to hold the cervical cap in position during strenuous activity thereby resulting in effective birth control. In addition, the novel conforming cervical cap is more comfortable to wear and provides freedom from systemic side effects which may occur from other prior cervical caps. Also, the novel cervical cap is formed of an elastomeric material which has substantially the same modulus of elasticity as human flesh. This provides a cervical cap with extreme flexibility and conformation and results in a cervical cap which cannot be easily dislodged from the exocervix during strenuous activity.

The novel method of forming a removable elastomeric cervical cap includes expanding the vaginal wall to expose the exocervix surface. A layer of a liquid self-curing elastomeric material is then applied to only the exocervix surface and permitted to solidify without distorting the surface. By applying a layer of a liquid self curing elastomeric material directly to the exocervix, distortion and deformation of the exocervix does not substantially occur and an identical negative-image conforming surface is obtained. In the novel method the final cervical cap is formed directly on the human female. The novel method can be completely performed without anesthesia with substantially no discomfort in about 10 minutes thereby providing an economical method to achieve birth control.

THE CERVICAL CAP

Figure 1:
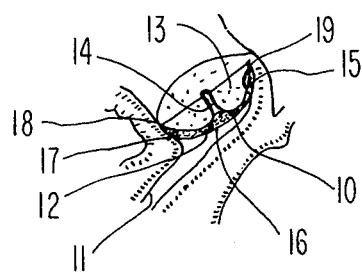
FIG. 1 is a sectional view of the novel cervical cap.

FIG. 1 illustrates in section view a novel cervical cap 10 positioned within the vagina 11 of a human female. The cap 10 is positioned over the surface 12 of the exocervix 13 to close the opening 14 thereof thereby preventing sperm transport therethrough.

The novel cervical cap 10 is a cap shaped member 15 of substantially hemispherical end surface 16 and a peripheral sidewall 17. The sidewall 17 ends in a rounded edge 18. It is preferred that the wall thickness is in the range of 1 to 7 mm (0.039 to 0.276 inches). The novel cervical cap 10 also has an inside surface 19 which conforms identically to the surface 12. The identical conformity permits a layer of cervical mucus to form between the cervical cap 10 and the exocervix 13 to assist in maintaining the cervical cap 10 in position on the exocervix 13. The novel cervical cap 10 also may include a valve member as will be disclosed.

In the preferred embodiment, the novel cervical cap 10 is formed of an elastomeric material. The preferred elastomeric material is a medical grade silicone rubber. One suitable silicone rubber is Silastic No. 382 Medical Grade Elastomer catalyzed for cross linking with Catalyst M (stannous octoate), both marketed by Dow Corning Corp. In the preferred embodiment the Silastic No. 382, having a viscosity of approximately 500 poises may be reduced by the addition of No. 360 Medical Fluid, marketed by Dow Corning Corp. The elastomeric material also may be thickened (made paste-like) with respect to flow at low shear rates by the addition of small quantities of ultra-fine silica such as Cab-O-Sil. This composition is then mixed with about 1% Catalyst M prior to or simultaneously with use. After addition of the catalyst the composition cures to a rubbery solid in about four minutes. The modulus of elasticity of the resulting solid is substantially the same as that of the cervical soft tissue.

THE VALVE MEMBER

Figure 2:
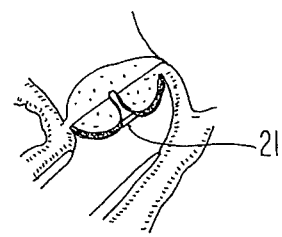
FIG. 2 is a sectional view of an alternative embodiment of the novel cervical cap shown in FIG. 1 illustrating a check-valve member therein.
Figure 3:
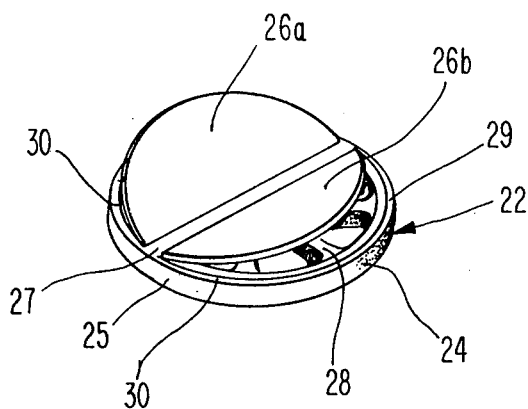
FIGS. 3 and 4 illustrate check-valve members for use in the novel cervical cap.
Figure 4:
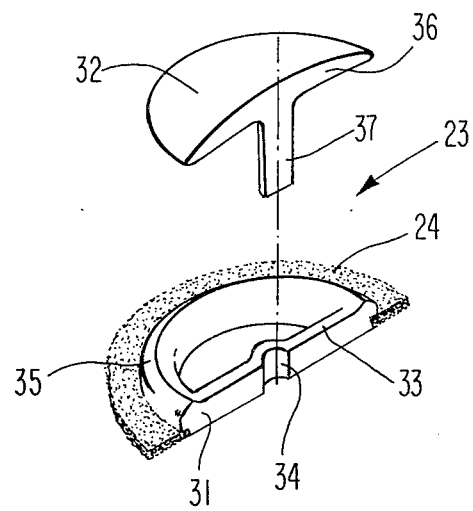

In another embodiment shown in FIG. 2, the novel cervical cap 10 also includes a valve member 21 integral therein. The valve member 21 includes a one-way valve or check-valve positioned substantially centered on the hemispherical end surface 16 of the cervical cap 10. The check-valve may be a "hinged leaflet" check-valve 22 as shown in FIG. 3 or a "mushroom" check-valve 23 as shown in FIG. 4.

The valve member 21 also includes an attachment portion 24 for attachment of the valve member 21 and the surrounding portion of the cervical cap 10. It is preferred that the attachment portion 24 is an outer ring of fabric such as nylon, although any perforated or porous biologically compatible material which permits sealing adherence to the material of the cervical cap 10 may also be used.

The check-valve 22 or 23, each include a sharp knife-edge line-contact sealing surface as will be disclosed. With a knife-edge sealing surface, high fluid shearing stresses can be obtained with a low closing force. This permits a physical cutting of the cervical mucus fluid stream with a low valve closing force. It is extremely important to cut the fluid mucus stream to prevent sperm transport and the possibility of a subsequent pregnancy. Prior check-valves used in a cervical cap, such as disclosed in U.S. Pat. No. 2,836,177 do not have a knife edge to physically cut the cervical mucus stream, therefore male sperm may pass up the fluid stream through the valve.

The check-valve 22 or 23 is normally closed to provide a positive cut-off of the cervical mucus stream. The check-valve opens only to permit excess fluid flow from the oviduct opening 14 into the vagina 11. The check-valve must also have a low opening resistance to permit fluid flow from the exocervix 13 for a small pressure differential. The cervical cap 10 with the integral valve member 21 permits easier insertion since air or fluids trapped under the cap may bleed out through the check-valve during insertion.

In the preferred embodiments the hinged leaflet check-valve 22 and the mushroom check-valve 23 are all molded of the medical grade silicone rubber previously disclosed.

The bodies of the check valves 22 and 23 also may be injection molded of a psysiologically inert thermoplastic. The leaflet and mushroom portions of the check-valve also may be molded of silicone rubber, ethylene-vinyl acetate copolymer, or a thermoplastic rubber. In addition the leaflets may be reinforced with a Dacron mesh to provide higher tear strength and rigidity.

The hinged leaflet check-valve 22 shown in FIG. 3 includes a body 25 and two valve leaflets 26a and 26b. The body 25 includes a central cross strut 27, a leaflet support 28 and a sealing surface 29. The two valve leaflets 26a and 26b are formed in a shape which forces them against the sealing surface 29. The sealing surface 29 includes a sharp knife-edge 30 to seal against the leaflets 26a and 26b. The knife edge 30 is V-shaped and formed with an included angle in the range of 20° to 160°. The preferred included angle is about 30°.

The two valve leaflets 26a and 26b remain normally closed against the sealing surface 29 except when an appropriate internal differential pressure is applied at which time cervical mucus drainage occurs.

The mushroom check valve 23 shown in FIG. 4 includes a body 31 and a mushroom shaped sealing member 32. The body 31 includes a cross strut 33 having a central opening 34 therein and a knife-edge peripheral sealing surface 35. The preferred knife edge sealing surface 35 is V-shaped with an included angle of about 30°. The mushroom shaped sealing member 32 includes a top 36 and a stem 37. The stem 37 is positioned within the opening 34 with the top 36 closing and sealing against the sealing surface 35. The top 36 remains closed against the sealing surface 35 except when a desired internal pressure occurs. The knife-edge peripheral sealing surface may also be on the top 36.

THE NOVEL METHOD

The novel cervical cap 10 may be made by the methods described in the following Examples 1 through 5. It is preferred that the cervical cap 10 be made at or near the fertile time of the female menstrual cycle since at this time the exocervix is considered to have its normal shape and this time requires the most protection. At other times in the menstrual cycle, the exocervix 13 may slightly change in dimension and shape.

Figure 5:
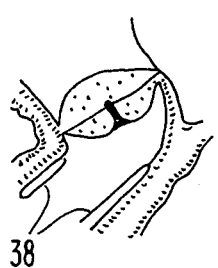
FIGS. 5, 6 and 7 illustrate steps in the novel method of Example 1.

Example 1: In the preferred method of nonsurgically forming the novel cervical cap 10, the wall of the vaginal 11 is initially expanded with vaginal speculum blades 38 to substantially expose therein the exocervix 13 as shown in FIG. 5.

Figure 6:
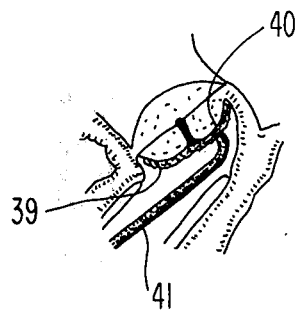

Then a liquid self-curing elastomeric material is applied over the surface 12 to form a layer 39 thereon as shown in FIG. 6. The preferred elastomeric material is the medical grade silicone rubber previously disclosed. Since the layer 39 is applied directly to the surface 12, the inside surface 40 thereof conforms identically thereto.

Figure 7:
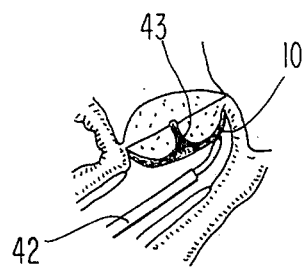

Although the self-curing elastomeric material is described as a liquid, in its preferred form it is paste-like and will flow only under pressure. The elastomeric material is applied by injection from a nozzle 41 or other similar device which is positioned through the vagina 11 as shown in FIG. 6. The nozzle 41 is supplied with the elastomeric material from a non-air entraining mixer and dispenser (not shown). When a nozzle 41 is used, it is manually moved over the surface of the exocervix 13 while dispensing the elastomeric material to provide the layer 39 thereon. Since the layer 39 formed may be non-uniform in thickness, the surface thereof may optionally be smoothed with an ice tool 42 inserted through the vagina 11 as shown in FIG. 7. The smoothing may also be accomplished using a wet wooden tool which has been allowed to soak in water for an extended period of time. It must be noted that the liquid elastomeric material is flexible and can easily conform to the identical surface of the exocervix 13 without distorting the exocervix 13. Therefore, an identical negative-image inner surface is formed in the cervical cap 10. The liquid elastomeric material is then allowed to cure and solidify. This occurs, with minimal movement of the exocervix 13 and vaginal wall 15, in about 4 minutes.

Then, after the curing is complete, a cervical cap 10 is formed which conforms identically to the surface 12 of the exocervix 13. The identical conformation of the cervical cap 10 not only provides substantially 100 percent effective blockage of sperm movement into the exocervix 13 but also provides a cervical cap 10 which is comfortable to wear.

When it is described that the inner surface 19 of the cervical cap conforms to the surface 12, it is meant that the inner surface 19 conforms substantially to the exposed surface surrounding the opening 14 in the exocervix 13. Typically, the opening 14 is filled with a plug 43 of cervical mucus (shown in FIG. 5). The central portion of the cervical cap 10 conforms or bridges over the plug 43 (shown in FIGS. 6 and 7). If the mucus plug is removed prior to making the cervical cap 10, the conformed cervical cap contains a cusp-like projecting member (not shown) which conforms to a portion of the uterine opening 14. This projecting member can be removed as desired from the finished cervical cap 10. It is preferred that the plug 43 be permitted to remain in place in the novel methods described in Examples 1 through 5.

Figure 8:
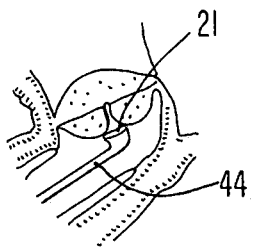
FIGS. 8, 9 and 10 illustrate steps in the novel method of Example 2.

Example 2. The wall of the vagina is expanded with the vaginal speculum blades 38 as disclosed in Example 1. A check valve member 21 is positioned with a vacuum tool 44 substantially centered over the uterine opening 14 as shown in FIG. 8.

Figure 9:
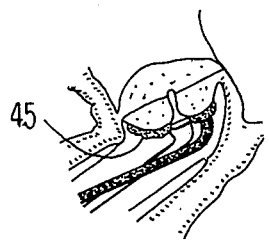

A layer 45 of a liquid self curing elastomeric material is applied to the surface 12 of the exocervix 13 surrounding the valve member 21 as shown in FIG. 9. The layer 45 partially penetrates and adheres to the attachment portion 24 of the valve member 21. The inside surface 46 of the layer 45 conforms identically to the surface 12 of the exocervix 13 except for the portion of the surface 12 covered by the valve member 21.

Figure 10:
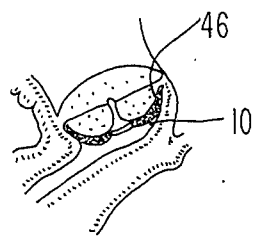

The layer 45 of liquid elastomeric material is then allowed to cure and solidify to form the removable cervical cap 10 with valve member 21 as shown in FIG. 10. The cured cervical cap 10 is flexible and can be easily removed and replaced. When the solidified cervical cap 10 is first removed, any uneven edges or surfaces can be smoothed as desired.

Figure 11:
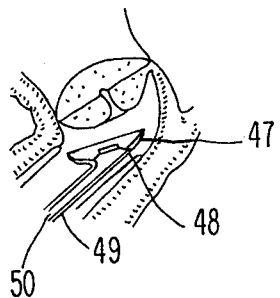
FIGS. 11, 12 and 13 illustrate steps in the novel method of Example 3.

Example 3. A preformed member 47 as shown in FIG. 11 is provided having a cap or concave shape similar to the shape of the surface 12 of the exocervix 13. The preformed member 47 includes support means 48 therein for holding a valve member 21 therein. The preformed member 47 is positioned on a handle 49 having aperture means 50 therethrough for the supply of a liquid elastomeric material. It is preferred that the preformed member 47 be made of silicone rubber as previously disclosed.

The method includes positioning a valve member 21 in the preformed member 47 and attaching the handle 49 thereto. The wall of the vagina 11 is expanded with the speculum blades 38 as previously disclosed to expose the exocervix 13.

Figure 12:
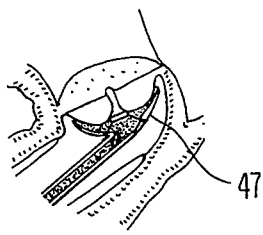
Figure 13:
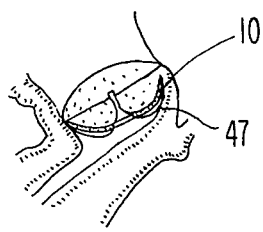

The preformed member 47 with the valve member 21 therein, is positioned and spaced from the exocervix 13 a distance of about 1/32 to 1/16 inch. This space occurs when the valve member 21 is in contact with the exocervix 13. Then a liquid self-curing elastomeric material is injected through the aperture means 50 to fill the space between the preformed member 47, the exocervix 13, and the valve member 21 as shown in FIG. 12. During the injection step, the working parts of the valve may be protected with a layer of release agent or a paper covering to prevent damage from the curing silicone rubber. The liquid elastomeric material is then allowed to cure and solidify. In curing, the liquid elastomeric material adheres to both the valve member and the preformed member to form a composite cervical cap 10 as shown in FIG. 13.

Example 4. A shell member 51 having a cap or concave shape similar to the shape of the exocervix 13 is provided. The shell member 51 includes a valve member 21 formed therein. The valve member 21 may be molded integrally with the shell member 51 or may be adhesively attached thereto.

Figure 14:
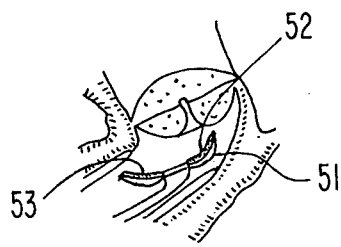
FIGS. 14 and 15 illustrate steps in the novel method of Example 4.

The method includes applying a layer 52 of soft paste-like self curing elastomeric material, such as previously disclosed, to the concave inner surface 53 of the shell member 51, the material surrounding the valve member 21 as shown in FIG. 14.

Figure 15:
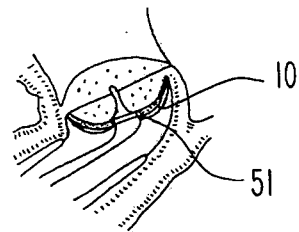

The wall of the vagina 11 is expanded to expose therein the surface 12 of the exocervix 13. The shell member 51 with the layer 52 thereon is positioned against the exocervix 13 as shown in FIG. 15. Sufficient pressure is used only to cause the elastomeric material to flow and conform to the identical shape of the surface 12 without distorting the shape of the surface 12.

The layer 52 is then allowed to cure and solidify. During the curing the elastomeric material adheres to the shell member 51 to form the cervical cap 10.

Figure 16:
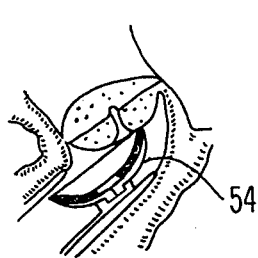
FIGS. 16, 17 and 18 illustrate steps in the novel method of Example 5.

Example 5. A split mold 54 as shown in FIG. 16 is provided. The split mold 54 includes support means 55 for holding a valve member 21. The split mold 54 must be formed of a material which is non adherent to the elastomeric material of the cervical cap 10. A preferable material for the split mold 54 is polyurethane.

Figure 17:
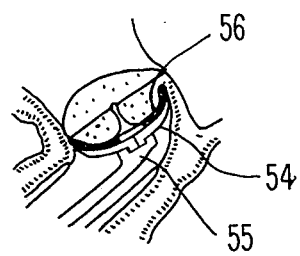
Figure 18:
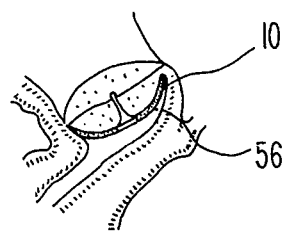

The valve member 21 is positioned in the split mold 54. The wall of the vagina 11 is expanded as previously disclosed to expose the exocervix 13. The split mold 54 is lined with a layer 56 of a liquid self-curing elastomeric material, as previously disclosed, and then it is firmly forced against the surface 12 as shown in FIG. 17 sufficient to conform the inner surface of the layer 56 to the surface 12 without distortion of the surface 12. The liquid elastomeric material is then allowed to cure and solidify to form the cervical cap 10. The split mold 54 is then removed to leave the cured cervical cap 10 in position on the exocervix 13 as shown in FIG. 18. It is preferred that a split mold 54 is used to permit the removal thereof while leaving the cervical cap 10 within the vagina 11.

REINSERTION REALIGNMENT

Figure 19:
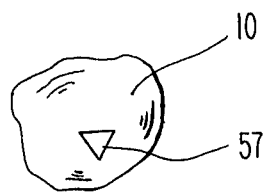
FIG. 19 illustrates the novel cervical cap of FIG. 1 having alignment means integral therein.

In a separate embodiment of each of the methods of Examples 1 through 5, visual tactile marking is formed on the outside surface of the cervical cap 10 to facilitate removal and reinsertion in the proper negative-image conforming alignment with the exocervix 13. The marking may take different forms. One form is merely an arrow 57 shaped projection placed at the front edge during forming as shown in FIG. 19. Another form is a line or other depression formed in the outer surface of the cervical cap 10. It must be understood that the marking is for rough alignment only, that the actual desired position will be finalized by the exact negative-image conformity of the surface 12 of the exocervix 13 with the inside surface 19 of the novel cervical cap 10, as well as the learned comfort experience of the user.

I claim:
1. The method of nonsurgically forming a removable cervical cap comprising the steps of
   a. expanding the vaginal wall to expose therein the exocervix surface, b. applying a flowable self-curing elastomeric material to form a layer on said exposed exocervix surface, the cured elastomeric material conforming substantially identically to the exocervix surface without substantial distortion and deformation of the exocervix surface and providing the cervical cap for blocking the entrance to the exocervix.

2. The method of nonsurgically forming a removable cervical cap comprising the steps of
   a. expanding the vaginal wall to expose therein the exocervix surface,
   b. positioning a check-valve member substantially centered over the exocervix surface,
   c. applying a flowable self-curing elastomeric material on the exposed exocervix surface without substantial distortion and deformation of the exocervix surface to form a layer thereon surrounding said check-valve member,
   d. and then permitting said elastomeric material to cure and solidify, and adhere to said check-valve member.

3. The method defined in claim 2 wherein said check-valve member s formed of a elastomeric material and includes peripheral attachment means, and wherein step (d) comprises allowing said self-curing elastomeric material to solidify and adhere to said attachment means to form a composite cervical cap and valve member.

4. In a method of nonsurgically forming a removable ceverical cap, the steps comprising
   a. expanding the vaginal wall to expose therein the exocervix surface,
   b. positioning a check-valve member having surrounding attachment means thereon substantially centered over the uterine opening,
   c. applying a layer of self-curing flowable elastomeric material on the exocervix surface without substantial distortion and deformation of the exocervix surface surrounding said check-valve member,
   d. and then permitting said elastomeric material to cure and adhere to said valve member to form a removable cervical cap, the elastomeric maaterial substantially conforming to the shape of the portion of said exocervix surface to which the elastomeric material is applied.

5. The method of nonsurgically forming a removable cervical cap comprising the steps of
   a. providing a preformed member having a shape similar to the shape of an exocervix surface, said member supporting a check-valve member therein,
   b. applying a layer of a self-curing elastomeric material to the concave surface of said preformed member and surrounding said check-valve member,
   c. expanding the vaginal wall to substantially expose the exocervix surface,
   d. positioning said preformed member with said elastomeric material thereon adjacent said exocervix surface,
   e. pressing said preformed member toward said exocervix surface to force said elastomeric material to contact and conform to the shape of the exocervix surface contacted without substantial distortion and deformation of the exocervix surface,
   f. then allowing said elastomeric material to solidify and adhere to said preformed member whereby said check-valve member, said preformed member and said cured elastomeric member form a removable cervical cap.

6. The method of nonsurgically forming a removable cervical cap comprising the steps of
   a. providing a mold having a shape substantially similar to the shape of an exocervix surface, said mold having means therein for supporting a check-valve member and aperture means therein the introducing a supply of flowable elastomeric material,
   b. positioning a check-valve member in said mold,
   c. expanding the vaginal wall to substantially expose said exocervix surface,
   d. positioning said mold with said check-valve member therein adjacent said exocervix surface with said check-valve member contacting said exocervix surface,
   e. injecting through said aperture means a flowable self-curing elastomeric material to fill the space between said mold, said exocervix surface, and said check-valve member, without substantial distortion and deformation of the exocervix surface.
   f. then permitting said elastomeric material to solidify and adhere to said check-valve member to form said cervical cap,
   g. and then removing said mold from said cervical cap.

7. The method of claim 1 wherein the elastomeric material is provided by silicone rubber.

8. The method of claim 4 wherein the check-valve member is formed of elastomeric material to which said applied elastomeric material adheres.

9. The method of claim 5 wherein the check-valve member and preformed member are formed of elastomeric material.

10. The method of claim 6 wherein the mold is made of a material that is nonadherent to the elastomeric material.

11. The method of claim 10 wherein the mold is made of polyurethane.

12. The method of claim 6 wherein the mold is split to form at least two pieces to permit removal of the mold from the formed cervical cap.

13. The method of nonsurgically forming a removable cervical cap comprising the steps of
   a. providing a mold having a shape substantially similar to the shape of an exocervix surface, said mold having support means therein for supporting a check-valve member,
   b. positioning a check-valve member on said support means,
   c. applying a layer of self-curing elastomeric material to the concave surface of said mold and surrounding said check-valve member,
   d. expanding the vaginal wall to expose said exocervix surface,
   e. positioning said mold with said elastomeric material thereon adjacent said exocervix surface,
   f. pressing said mold toward said exocervix surface to force said elastomeric material to contact and conform to the shape of the exocervix surface contacted without substantial distortion and deformation of the exocervix surface,
   g. permitting said elastomeric material to solidify and adhere to said check-valve member to form said cervical cap,
   h. and removing said mold from said cervical cap.

* * * * *